United States Patent
Fredrick et al.

(10) Patent No.: US 12,213,834 B2
(45) Date of Patent: Feb. 4, 2025

(54) ULTRASOUND TRANSDUCER WITH ACOUSTIC ABSORBER STRUCTURE

(71) Applicant: Exo Imaging, Inc., Redwood City, CA (US)

(72) Inventors: Daniela Marisa Fredrick, Auburn, CA (US); Charles Baumgartner, Niskayuna, NY (US); Brian Lee Bircumshaw, Oakland, CA (US); Joseph Michael Adam, Truckee, CA (US)

(73) Assignee: Exo Imaging, Inc., Santa Clara, CA (US)

( * ) Notice: Subject to any disclaimer, the term of this patent is extended or adjusted under 35 U.S.C. 154(b) by 892 days.

(21) Appl. No.: 16/953,072

(22) Filed: Nov. 19, 2020

(65) Prior Publication Data

US 2021/0153844 A1    May 27, 2021

Related U.S. Application Data (60) Provisional application No. 62/939,262, filed on Nov. 22, 2019.

(51) Int. Cl.
    *A61B 8/00* (2006.01)

(52) U.S. Cl.
    CPC .......... *A61B 8/4444* (2013.01); *A61B 8/4483* (2013.01); *A61B 8/546* (2013.01); *C08J 2205/00* (2013.01)

(58) Field of Classification Search
    CPC ........... A61B 8/44; A61B 8/46; A61B 8/4483; A61B 8/4494; A61B 2090/0436; A61B 2090/0445
    See application file for complete search history.

(56) References Cited

U.S. PATENT DOCUMENTS

| 4,511,052 A | 4/1985 | Klein et al. |
| 5,127,410 A | 7/1992 | King et al. |
| 5,810,733 A | 9/1998 | Van et al. |
| 6,958,255 B2 | 10/2005 | Khuri-Yakub et al. |
| 8,988,971 B2 | 3/2015 | Mueller et al. |
| 9,067,779 B1 | 6/2015 | Rothberg et al. |
| 2003/0235119 A1 | 12/2003 | Wien et al. |

(Continued)

FOREIGN PATENT DOCUMENTS

| CN | 106536067 A | 3/2017 |
| CN | 107768335 A | 3/2018 |

(Continued)

OTHER PUBLICATIONS

PCT/US2022/012126 International Search Report and Written Opinion dated Apr. 1, 2022.

(Continued)

*Primary Examiner* — Walter L Lindsay, Jr.
*Assistant Examiner* — Andrew V Do
(74) *Attorney, Agent, or Firm* — Morgan, Lewis & Bockius LLP (57) ABSTRACT

Described are acoustic absorber materials with high acoustic attenuation and high thermal conductivity comprising an inorganic, porous foam and an absorbing material within at least a portion of the pores of the foam, ultrasound transducers and devices including the same, as well as methods of making the materials.

25 Claims, 6 Drawing Sheets

(56) References Cited

U.S. PATENT DOCUMENTS

| | | |
|---|---|---|
| 2004/0085858 A1 | 5/2004 | Khuri-Yakub et al. |
| 2007/0239001 A1 | 10/2007 | Mehi et al. |
| 2007/0299345 A1 | 12/2007 | Adachi et al. |
| 2008/0194053 A1 | 8/2008 | Huang |
| 2008/0296708 A1 | 12/2008 | Wodnicki et al. |
| 2009/0001853 A1 | 1/2009 | Adachi et al. |
| 2009/0122651 A1 | 5/2009 | Kupnik et al. |
| 2009/0140609 A1 | 6/2009 | Huang |
| 2010/0168583 A1 | 7/2010 | Dausch et al. |
| 2011/0115333 A1 | 5/2011 | Ezaki |
| 2011/0218594 A1 | 9/2011 | Doron et al. |
| 2012/0068571 A1 | 3/2012 | Chen |
| 2012/0238880 A1 | 9/2012 | Davidsen |
| 2012/0277639 A1 | 11/2012 | Pollock et al. |
| 2013/0020698 A1 | 1/2013 | Hsieh et al. |
| 2013/0345567 A1 | 12/2013 | Sudol et al. |
| 2014/0035735 A1 | 2/2014 | Zellers et al. |
| 2014/0184027 A1 | 7/2014 | Rice et al. |
| 2014/0187962 A1 | 7/2014 | Reiter |
| 2014/0220723 A1 | 8/2014 | Liu et al. |
| 2015/0061465 A1 | 3/2015 | Lee et al. |
| 2015/0087991 A1 | 3/2015 | Chen et al. |
| 2015/0097468 A1 | 4/2015 | Hajati et al. |
| 2015/0145374 A1 | 5/2015 | Xu et al. |
| 2015/0282783 A1 | 10/2015 | Katsura et al. |
| 2016/0007961 A1* | 1/2016 | Lee .................. B05D 1/18 600/459 |
| 2016/0009544 A1 | 1/2016 | Rothberg et al. |
| 2016/0045935 A1 | 2/2016 | Yoon et al. |
| 2016/0187301 A1 | 6/2016 | Gu |
| 2017/0232474 A1 | 8/2017 | Oralkan et al. |
| 2018/0003678 A1 | 1/2018 | Rothberg et al. |
| 2018/0153510 A1 | 6/2018 | Haque et al. |
| 2019/0015072 A1 | 1/2019 | Deladi et al. |
| 2019/0178849 A1 | 6/2019 | Abraham et al. |
| 2019/0316957 A1 | 10/2019 | Akkaraju et al. |
| 2021/0086231 A1 | 3/2021 | Bircumshaw et al. |
| 2021/0088655 A1 | 3/2021 | Bircumshaw et al. |
| 2021/0094070 A1 | 4/2021 | Bircumshaw et al. |

FOREIGN PATENT DOCUMENTS

| | | |
|---|---|---|
| EP | 1992290 A1 | 11/2008 |
| EP | 1436097 B1 | 2/2016 |
| JP | 2004130138 A | 4/2004 |
| JP | 2007229327 A | 9/2007 |
| JP | 2017528940 A | 9/2017 |
| JP | 2018029147 A | 2/2018 |
| KR | 20160018235 A | 2/2016 |
| KR | 20170030605 A | 3/2017 |
| WO | WO-2008137030 A1 | 11/2008 |
| WO | WO-2016011000 A1 | 1/2016 |
| WO | WO2016054447 A1 | 4/2016 |
| WO | WO-2017143307 A1 | 8/2017 |
| WO | WO-2019222116 A1 | 11/2019 |
| WO | WO-2019222118 A1 | 11/2019 |
| WO | WO-2020198257 A1 | 10/2020 |
| WO | WO-2021102127 A1 | 5/2021 |

OTHER PUBLICATIONS

PCT/US2020/061261 International Search Report and Written Opinion dated Feb. 9, 2021.

Mahn et al. Au—Sn solid-liquid interdiffusion (SLID) bonding for piezoelectric ultrasonic transducers. 2016 IEEE International Ultrasonics Symposium (IUS) Tours (pp. 1-4)(2016).

PCT/US2019/032060 International Search Report and Written Opinion dated Jul. 26, 2019.

PCT/US2019/032062 International Search Report and Written Opinion dated Jul. 29, 2019.

PCT/US2021/056026 International Search Report and Written Opinion dated Jan. 28, 2022.

PCT/US2021/056669 International Search Report and Written Opinion dated Jan. 28, 2022.

PCT/US2022/021556 International Search Report and Written Opinion dated Jul. 22, 2022.

PCT/US2022/021556 Invitation to Pay Additional Fees dated May 26, 2022.

* cited by examiner

ULTRASOUND TRANSDUCER WITH ACOUSTIC ABSORBER STRUCTURE

CROSS-REFERENCE TO RELATED APPLICATIONS

This application claims the priority and benefit of U.S. Provisional Application No. 62/939,262, filed Nov. 22, 2019, the entire content of which is incorporated herein by reference in its entirety.

BACKGROUND

Ultrasound acoustic arrays convert electrical energy to acoustic energy and transmit the acoustic energy towards a patient being scanned to obtain imaging data from acoustic energy reflected off the anatomy of the patient.

SUMMARY

In one aspect, disclosed herein are thermally conductive acoustic absorbers for a transducer, the acoustic absorber comprising: a porous foam having a plurality of pores; and an acoustic absorbing material disposed within at least one or at least a portion of the plurality of pores of the porous foam. In some embodiments, the pores form a continuous network. In other embodiments, the pores form a semi-continuous network. In some embodiments, the pores are partially closed. In some embodiments, the pores are stochastic. In other embodiments, the pores are regular. In some embodiments, the porous foam has a pore density of about 2 pores/cm to about 50 pores/cm. In some embodiments, the porous foam has a porosity of about 60% to about 98%. In some embodiments, the porous foam comprises a cellular material, a sponge material, or both. In some embodiments, the porous foam comprises an inorganic material with a porous foam structure. In some embodiments, the inorganic material comprises a metal, a metal alloy, a ceramic, a semiconductor, a composite, or any combination thereof. In some embodiments, the inorganic material is at least partially crystalline. In some embodiments, the inorganic material comprises a metal or a metal alloy. In various further embodiments, the metal or the metal alloy comprises cobalt, gold, iron, iron chromium, nickel, lead, nickel chromium, nickel iron chromium, silver, tantalum, tungsten, zirconium, aluminum, copper aluminum, molybdenum, nickel copper, nickel iron, rhenium, stainless steel, tin, tungsten nickel, zirconium, cadmium, cobalt chromium, copper, iron chromium aluminum, lanthanated molybdenum, nickel magnesium gallium, titanium, tantalum zirconium molybdenum, or any combination thereof. In some embodiments, wherein the inorganic material comprises a ceramic. In various further embodiments, the ceramic comprises an oxide, a carbide, a nitride, a silicate, or any combination thereof. In still further embodiments, the ceramic comprises an oxide, and the oxide comprises aluminum oxide, zinc antimony bismuth oxide, or a combination thereof. In still further embodiments, the ceramic comprises a carbide, and the carbide comprises boron carbide, zirconium carbide, hafnium carbide, tantalum carbide, zinc carbide, tungsten carbide, or a combination thereof. In still further embodiments, the ceramic comprises a nitride, and the nitride comprises boron nitride. In still further embodiments, the ceramic comprises carbon. In still further embodiments, the ceramic comprises yttria stabilized zirconia. In some embodiments, the inorganic material comprises a semiconductor. In various further embodiments, the semiconductor comprises silicon, silicon nitride, cadmium sulfide nickel, or a combination thereof. In some embodiments, the inorganic material comprises a composite, and the composite comprises a metal, a metal alloy, a semiconductor, or a combination thereof. In various further embodiments, the composite comprises carbon, silica, silicon, silicon nitride carbide, silicon oxy carbide, silicon carbide, cadmium sulfide nickel, alumina borosilicate, or a combination thereof. In some embodiments, the composite comprises fibers, particles, or both fibers and particles imparting higher thermal conductivity or mechanical strength. In some embodiments, the inorganic material is at least partially amorphous. In some embodiments, the inorganic material comprises a metal or a metal alloy, and the metal or the metal alloy comprises bulk metallic glass. In further embodiments, the bulk metallic glass comprises titanium, zirconium, or a combination thereof. In still further embodiments, the bulk metallic glass comprises ZrCuAlNiTi bulk metallic glass. In some embodiments, the inorganic material comprises a ceramic, and the ceramic comprises carbon, silicon oxy carbide, zinc doped borosilicate, glass, or a combination thereof. In some embodiments, the inorganic material comprises a ceramic, and the ceramic comprises glass, and the glass comprises silicon oxide, calcium carbon oxide, sodium carbon oxygen, or a combination thereof. In some embodiments, the inorganic material comprises a semiconductor, and the semiconductor comprises silicon, silicon nitride, or a combination thereof. In some embodiments, the inorganic material comprises a metal, a metal alloy, a ceramic, a composite, or any combination thereof, and one or more doping agents. In some embodiments, the acoustic absorbing material has an acoustic impedance different from that of the porous foam. In further embodiments, the acoustic absorbing material has an acoustic impedance lower (or significantly lower) than that of the porous foam. In some embodiments, the acoustic absorbing material comprises an inorganic material. In further embodiments, the acoustic absorbing material comprises a silicone. In still further embodiments, the silicone comprises a silicone-containing rubber. In still further embodiments, the silicone comprises polydimethylsiloxane, polyvinylmethylsiloxane, polyfluoromethylsiloxane, or a combination thereof. In some embodiments, the acoustic absorbing material comprises an organic material. In further various embodiments, the acoustic absorbing material comprises epoxy, polyurethane, polybutadiene rubber, or a combination thereof. In further various embodiments, the acoustic absorbing material comprises polyethylene, acrylic, polycarbonate, polystyrene, polysulphone, polyvinylchloride, or a combination thereof. In some embodiments, the acoustic absorbing material comprises a base material and an inorganic filler. In further embodiments, the inorganic filler is in the form of particles, platelets, needles, or a combination thereof. In some embodiments, the inorganic filler has an acoustic impedance different from that of the base material. In further embodiments, the inorganic filler has an acoustic impedance larger (or significantly larger) than that of the base material. In various embodiments, the inorganic filler comprises tungsten, tungsten carbide, aluminum oxide, aluminum nitride, hafnium oxide, barium oxide, tantalum, tantalum oxide, molybdenum, molybdenum oxide, chromium, chromium oxide, titanium dioxide, iron, iron oxide, cobalt, cobalt oxide, nickel, nickel oxide, copper, copper oxide, or a combination thereof. In some embodiments, the thermally conductive acoustic absorber has a ratio by volume of the acoustic absorbing material to the porous foam of about 1.5:1 to about 49:1. In some embodiments, the thermally conductive acoustic absorber has a thermal conductivity of at least 1 W/mK.

In another aspect, disclosed herein are ultrasound probes comprising: a printed circuit board (PCB); an application-specific integrated circuit (ASIC); an ultrasound transducer; and a thermally conductive acoustic absorber comprising: a porous foam having a plurality of pores; and an acoustic absorbing material disposed within at least one or at least a portion of the plurality of pores of the porous foam. In some embodiments, the pores form a continuous network. In other embodiments, the pores form a semi-continuous network. In some embodiments, the pores are partially closed. In other embodiments, the pores are closed. In some embodiments, the porous foam has a pore density of about 2 pores/cm to about 50 pores/cm. In some embodiments, the porous foam has a porosity of about 60% to about 98%. In some embodiments, the porous foam comprises a cellular material, a sponge material, or both. In some embodiments, the porous foam comprises an inorganic material with a porous foam structure. In further embodiments, the inorganic material comprises a metal, a metal alloy, a ceramic, a semiconductor, a composite, or any combination thereof. In some embodiments, the inorganic material is at least partially crystalline. In some embodiments, the inorganic material comprises a metal or a metal alloy. In various further embodiments, the metal or the metal alloy comprises cobalt, gold, iron, iron chromium, nickel, lead, nickel chromium, nickel iron chromium, silver, tantalum, tungsten, zirconium, aluminum, copper aluminum, molybdenum, nickel copper, nickel iron, rhenium, stainless steel, tin, tungsten nickel, zirconium, cadmium, cobalt chromium, copper, iron chromium aluminum, lanthanated molybdenum, nickel magnesium gallium, titanium, tantalum zirconium molybdenum, or any combination thereof. In some embodiments, the inorganic material comprises a ceramic. In further embodiments, the ceramic comprises an oxide, a carbide, a nitride, a silicate, or any combination thereof. In still further embodiments, the ceramic comprises an oxide, and the oxide comprises aluminum oxide, zinc antimony bismuth oxide, or a combination thereof. In still further embodiments, the ceramic comprises a carbide, and the carbide comprises boron carbide, zirconium carbide, hafnium carbide, tantalum carbide, zinc carbide, tungsten carbide, or a combination thereof. In still further embodiments, the ceramic comprises a nitride, and the nitride comprises boron nitride. In still further embodiments, the ceramic comprises carbon. In still further embodiments, the ceramic comprises yttria stabilized zirconia. In some embodiments, the inorganic material comprises a semiconductor. In further embodiments, the semiconductor comprises silicon, silicon nitride, cadmium sulfide nickel, or a combination thereof. In some embodiments, the inorganic material comprises a composite, and the composite comprises a metal, a metal alloy, a semiconductor, or a combination thereof. In various further embodiments, the composite comprises carbon, silica, silicon, silicon nitride carbide, silicon oxy carbide, silicon carbide, cadmium sulfide nickel, alumina borosilicate, or a combination thereof. In still further embodiments, the composite comprises fibers, particles, or both fibers and particles imparting higher thermal conductivity or mechanical strength. In some embodiments, the inorganic material is at least partially amorphous. In further embodiments, the inorganic material comprises a metal or a metal alloy, and the metal or the metal alloy comprises bulk metallic glass. In still further embodiments, the bulk metallic glass comprises titanium, zirconium, or a combination thereof. In still further embodiments, the bulk metallic glass comprises ZrCuAlNiTi bulk metallic glass. In some embodiments, the inorganic material comprises a ceramic, and the ceramic comprises carbon, silicon oxy carbide, zinc doped borosilicate, glass, or a combination thereof. In further embodiments, the inorganic material comprises a ceramic, and the ceramic comprises glass, and the glass comprises silicon oxide, calcium carbon oxide, sodium carbon oxygen, or a combination thereof. In some embodiments, the inorganic material comprises a semiconductor, and the semiconductor comprises silicon, silicon nitride, or a combination thereof. In some embodiments, the inorganic material comprises a metal, a metal alloy, a ceramic, a composite, or any combination thereof, and one or more doping agents. In some embodiments, the acoustic absorbing material has an acoustic impedance different from that of the porous foam. In further embodiments, the acoustic absorbing material has an acoustic impedance lower (or significantly lower) than that of the porous foam. In some embodiments, the acoustic absorbing material comprises an inorganic material. In further embodiments, the acoustic absorbing material comprises a silicone. In still further embodiments, the silicone comprises a silicone-containing rubber. In various further embodiments, the silicone comprises polydimethylsiloxane, polyvinylmethylsiloxane, polyfluoromethylsiloxane, or a combination thereof. In other embodiments, the acoustic absorbing material comprises an organic material. In further embodiments, the acoustic absorbing material comprises epoxy, polyurethane, polybutadiene rubber, or a combination thereof. In various further embodiments, the acoustic absorbing material comprises polyethylene, acrylic, polycarbonate, polystyrene, polysulphone, polyvinylchloride, or a combination thereof. In some embodiments, the acoustic absorbing material comprises a base material and an inorganic filler. In further embodiments, the inorganic filler is in the form of particles, platelets, needles, or a combination thereof. In some embodiments, the inorganic filler has an acoustic impedance different from that of the base material. In further embodiments, the inorganic filler has an acoustic impedance larger (or significantly larger) than that of the base material. In various further embodiments, the inorganic filler comprises tungsten, tungsten carbide, aluminum oxide, aluminum nitride, hafnium oxide, barium oxide, tantalum, tantalum oxide, molybdenum, molybdenum oxide, chromium, chromium oxide, titanium dioxide, iron, iron oxide, cobalt, cobalt oxide, nickel, nickel oxide, copper, copper oxide, or a combination thereof. In some embodiments, a ratio by volume of the acoustic absorbing material to the porous foam of about 1.5:1 to about 49:1. In some embodiments, the acoustic absorber has a thermal conductivity of at least 1 W/mK. In some embodiments, the acoustic absorber is mounted between the PCB and the ASIC. In some embodiments, the ultrasound probe further comprises a PCB heatsink coupled to the PCB, wherein the acoustic absorber is mounted between the PCB and the PCB heatsink. In some embodiments, the ultrasound probe comprises two or more acoustic absorbers, wherein at least one of the two or more acoustic absorbers is mounted between the PCB and the ASIC, and wherein at least one of the two or more acoustic absorbers is mounted between the PCB and the PCB heatsink. In some embodiments, the ultrasound transducer comprises a Piezoelectric Micromachined Ultrasonic Transducer. In other embodiments, the ultrasound transducer comprises a Capacitive Micromachined Ultrasonic Transducer.

In yet another aspect, disclosed herein are methods of forming a thermally conductive acoustic absorber for an ultrasound transducer, the method comprising: receiving a porous foam having a plurality of pores; and at least partially saturating at least a portion of the plurality of pores of the porous foam with an acoustic absorbing material. In various embodiments, the at least partially saturating at least a portion of the pores of the porous foam with an acoustic absorbing material comprises: drawing the acoustic absorbing material into the plurality of pores of the porous foam under vacuum; pressing the acoustic absorbing material into the plurality of pores of the porous foam under pressure; or both drawing the acoustic absorbing material into the plurality of pores of the porous foam under vacuum and pressing the acoustic absorbing material into the plurality of pores of the porous foam under pressure.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Ultrasound imagers comprise an acoustic transducer or Micromachined Ultrasound Transducer (MUT) mounted to an Application-Specific Integrated Circuit (ASIC or acoustic tile), wherein the MUT converts electrical energy to acoustic energy and transmits the acoustic energy towards a patient being scanned. A portion of the energy reflects of the anatomy of the patient to produce an ultrasound image.

As such ASICs generate significant heat during operation, the FDA has placed temperature limits on the surface of the medical ultrasound transducers to prevent patient injury. Currently, heat from the ASIC is absorbed by a metallic heatsink mounted to the ASIC and in contact with a printed circuit board (PCB). However, reflection of acoustic energy off the metallic heatsink from behind the acoustic transducer can degrade the imaging data. While some medical ultrasound imaging transducers implement a rubber or epoxy-based acoustic absorbing material mounted to the metallic heatsink to reduce such degradation, such acoustic absorbing material reduces the efficacy of the heatsink to remove heat from the ASIC, such that the FDA temperature limitations are surpassed.

Provided herein are thermally conductive acoustic absorbers for a transducer that act as an acoustic absorber and whose thermal conductivity is sufficient to act as a heatsink. Further, unlike the currently available rubber or epoxy-based acoustic absorbing materials, the acoustic absorbers described herein have sufficient strength and rigidity to allow direct connection and bonding to other electrical components. The thermally conductive acoustic absorbers described herein are suitable for various types of acoustic transducers, such as Micromachined Ultrasound Transducers (MUT), including Piezoelectric Micromachined Ultrasonic Transducers (PMUTs) and Capacitive Micromachined Ultrasonic Transducers (CMUTs).

Thermally Conductive Acoustic Absorber Material

Figure 1:
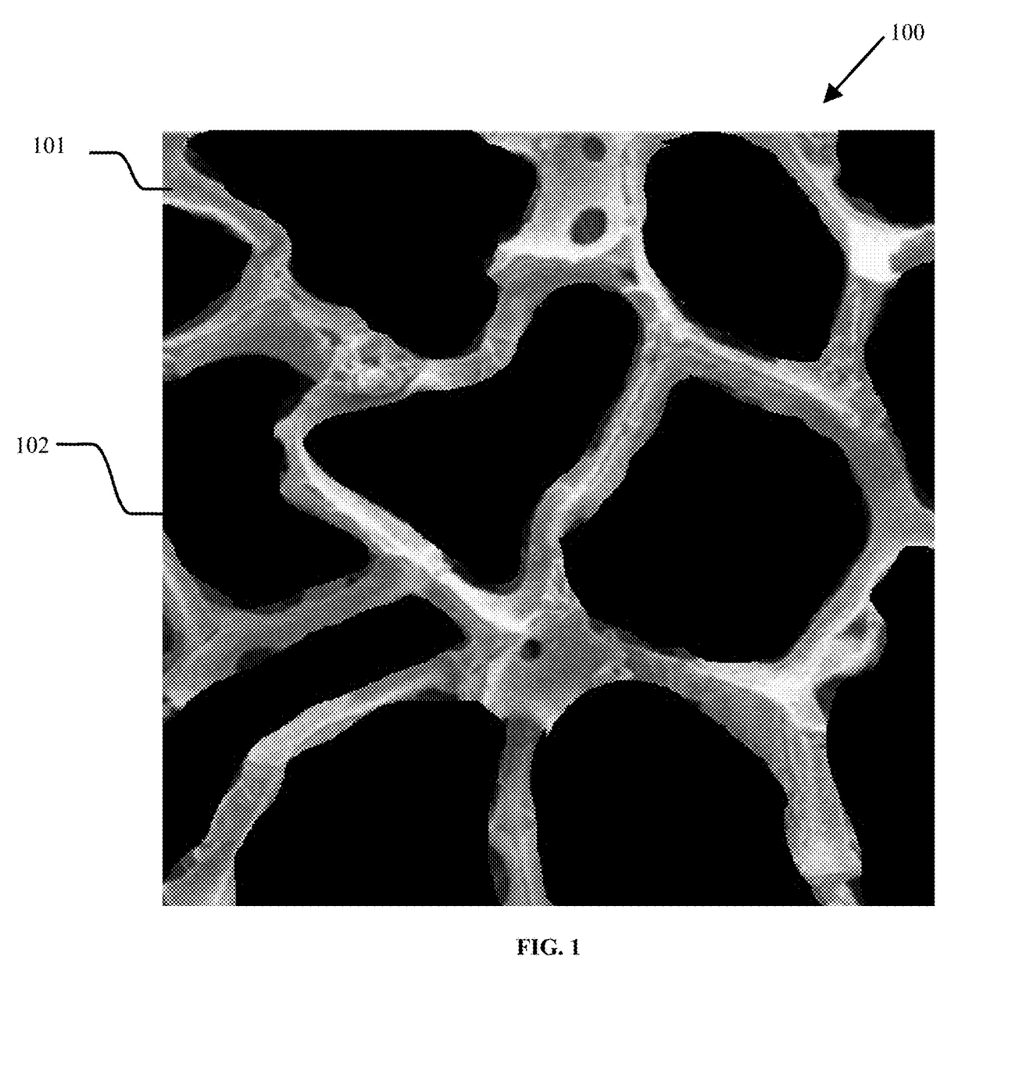
FIG. 1 shows an illustration of an exemplary acoustic absorbing material, per an embodiment herein.
Figure 2:
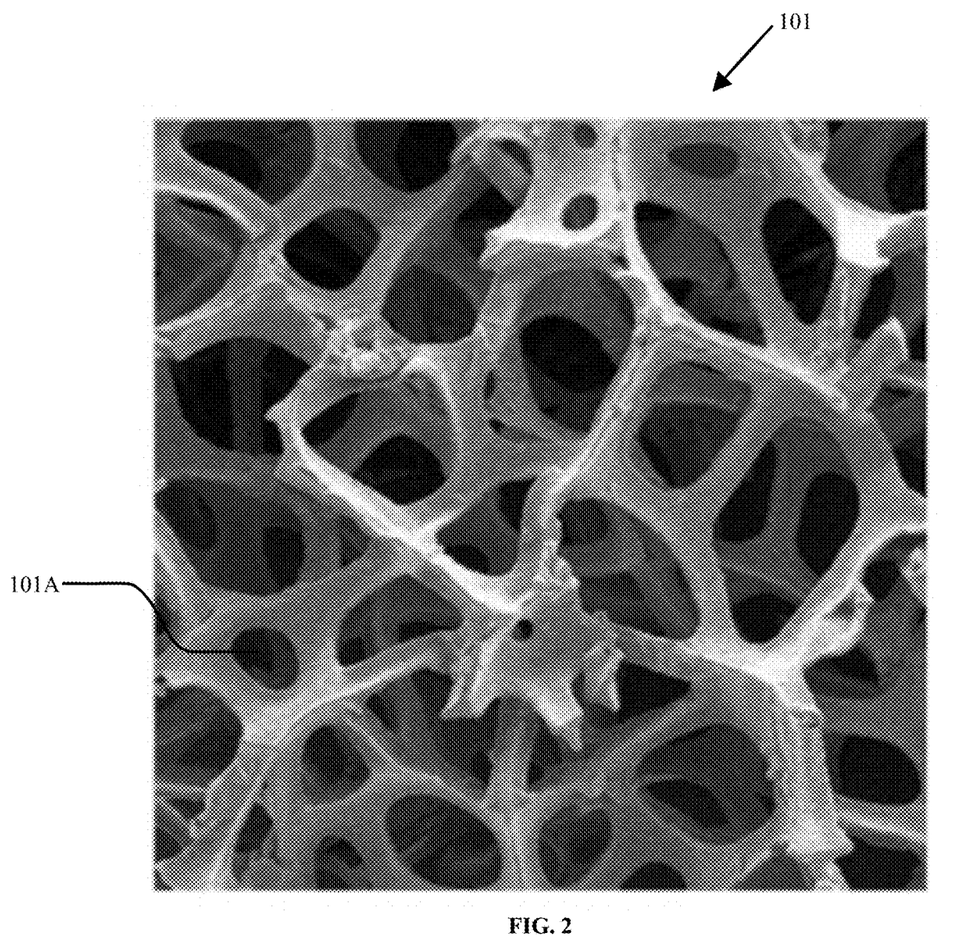
FIG. 2 shows an image of an exemplary porous foam, per an embodiment herein.

One aspect provided herein, per FIGS. 1-2 is a thermally conductive acoustic absorber 100 for a transducer. In some embodiments, the thermally conductive acoustic absorber 100 has both a high level of acoustic energy absorption and a high thermal conductivity. In some embodiments, the acoustic absorber 100 comprises a porous foam 101 and an acoustic absorbing material 102. In some embodiments, the porous foam 101 has a plurality of pores 101A. In some embodiments, the acoustic absorbing material 102 is displaced within the plurality of pores 101A of the porous foam 101. In some embodiments, the acoustic absorbing material 102 is displaced within at least a portion of plurality of pores 101A of the porous foam 101. In some embodiments, the acoustic absorbing material 102 is displaced within a majority of pores 101A of the porous foam 101. In some embodiments, the specific materials and structures of the porous foam 101 herein enables the high thermal conductivity of the acoustic absorber 100 whereas the acoustic absorbing material 102 provides the high acoustic attenuation.

In some embodiments, a thermal conductivity of the porous foam 101 is greater than a thermal conductivity of the acoustic absorbing material 102. In some embodiments, a thermal conductivity of the porous foam 101 is greater than a thermal conductivity of the acoustic absorbing material 102 by a factor of about 1.25, 1.5, 2, 3, 4, 5, 6, 7, 8, 9, 10, or more, including increments therein. In some embodiments, the thermal conductivity of the porous foam 101 is greater than the thermal conductivity of the acoustic absorbing material 102 by at least a factor of about 1.25, 1.5, 2, 3, 4, 5, 6, 7, 8, 9, or 10. In some embodiments, an acoustic impedance of the acoustic absorbing material 102 is less than an acoustic impedance of the porous foam 101 by a factor of about 1.25, 1.5, 2, 3, 4, 5, 6, 7, 8, 9, 10, 20, 30, 40, 50, or more, including increments therein. In some embodiments, the acoustic impedance of the acoustic absorbing material 102 is less than the acoustic impedance of the porous foam 101 by at least a factor of about 1.25, 1.5, 2, 3, 4, 5, 6, 7, 8, 9, 10, 20, 30, 40, 50, or more, including increments therein. In some embodiments, a large difference between the acoustic impedances of the acoustic absorbing material 102 and the porous foam 101 result in a high level of acoustic energy absorption and effective attenuation of acoustic energy reflected off structures located behind the acoustic transducer. Such acoustic energy absorption and attenuation reduces artifacts and enables collection of clear and accurate imaging data.

In some embodiments, a ratio by volume of the acoustic absorbing material 102 to the porous foam 101 is about 1.5:1 to about 49:1. In some embodiments, a ratio by volume of the acoustic absorbing material 102 to the porous foam 101 is about 1.5:1 to about 3:1, about 1.5:1 to about 5:1, about 1.5:1 to about 10:1, about 1.5:1 to about 15:1, about 1.5:1 to about 20:1, about 1.5:1 to about 25:1, about 1.5:1 to about 30:1, about 1.5:1 to about 35:1, about 1.5:1 to about 40:1, about 1.5:1 to about 45:1, about 1.5:1 to about 49:1, about 3:1 to about 5:1, about 3:1 to about 10:1, about 3:1 to about 15:1, about 3:1 to about 20:1, about 3:1 to about 25:1, about 3:1 to about 30:1, about 3:1 to about 35:1, about 3:1 to about 40:1, about 3:1 to about 45:1, about 3:1 to about 49:1, about 5:1 to about 10:1, about 5:1 to about 15:1, about 5:1 to about 20:1, about 5:1 to about 25:1, about 5:1 to about 30:1, about 5:1 to about 35:1, about 5:1 to about 40:1, about 5:1 to about 45:1, about 5:1 to about 49:1, about 10:1 to about 15:1, about 10:1 to about 20:1, about 10:1 to about 25:1, about 10:1 to about 30:1, about 10:1 to about 35:1, about 10:1 to about 40:1, about 10:1 to about 45:1, about 10:1 to about 49:1, about 15:1 to about 20:1, about 15:1 to about 25:1, about 15:1 to about 30:1, about 15:1 to about 35:1, about 15:1 to about 40:1, about 15:1 to about 45:1, about 15:1 to about 49:1, about 20:1 to about 25:1, about 20:1 to about 30:1, about 20:1 to about 35:1, about 20:1 to about 40:1, about 20:1 to about 45:1, about 20:1 to about 49:1, about 25:1 to about 30:1, about 25:1 to about 35:1, about 25:1 to about 40:1, about 25:1 to about 45:1, about 25:1 to about 49:1, about 30:1 to about 35:1, about 30:1 to about 40:1, about 30:1 to about 45:1, about 30:1 to about 49:1, about 35:1 to about 40:1, about 35:1 to about 45:1, about 35:1 to about 49:1, about 40:1 to about 45:1, about 40:1 to about 49:1, or about 45:1 to about 49:1. In some embodiments, a ratio by volume of the acoustic absorbing material 102 to the porous foam 101 is about 1.5:1, about 3:1, about 5:1, about 10:1, about 15:1, about 20:1, about 25:1, about 30:1, about 35:1, about 40:1, about 45:1, or about 49:1, including increments therein. In some embodiments, a ratio by volume of the acoustic absorbing material 102 to the porous foam 101 is at least about 1.5:1, about 3:1, about 5:1, about 10:1, about 15:1, about 20:1, about 25:1, about 30:1, about 35:1, about 40:1, or about 45:1, including increments therein. In some embodiments, a ratio by volume of the acoustic absorbing material 102 to the porous foam 101 is at most about 3:1, about 5:1, about 10:1, about 15:1, about 20:1, about 25:1, about 30:1, about 35:1, about 40:1, about 45:1, or about 49:1, including increments therein.

In various embodiments, the ratio by volume of the acoustic absorbing material 102 to the porous foam 101 is measured as an average ratio, a minimum ratio, or a maximum ratio.

Porous Foam

The specific structure and materials of the porous foam 101 herein provide enhanced thermal conductivity and plurality of pores 101A to contain the acoustic absorbing material 102. In some embodiments, the pores 101A of the porous foam 101 form a continuous network. In further embodiments, in the continuous network, at least a portion of the pores 101A are interconnected. In still further embodiments, in the continuous network, at least a majority of the pores 101A are interconnected. In some embodiments, in the continuous network, a plurality of pores 101A form a continuous channel through the porous foam 101. In other embodiments, the pores 101A form a closed network. In further embodiments, in the closed network, at least a portion of the pores 101A are isolated and closed. In still further embodiments, in the continuous network, at least a majority of the pores 101A are isolated and closed. In some embodiments, in the continuous network, a plurality of pores 101A do not form a continuous channel through the porous foam 101. In some embodiments, the pores 101A form a semi-continuous network. In some embodiments, in the semi-continuous network, at most a majority of the pores 101A are interconnected. In some embodiments, in the semi-continuous network, at least a portion of the pores 101A are closed and isolated. In some embodiments, the pores 101A are partially closed. In other embodiments, the pores 101A are open. In some embodiments, the pores 101A are stochastic. In other embodiments, the pores 101A are regular.

In some embodiments, the porous foam 101 comprises an inorganic material. In some embodiments, the inorganic material comprises a metal, a metal alloy, a ceramic, a semiconductor, a doping agent, or any combination thereof. In some embodiments, at least one of the metal, the metal alloy, and the ceramic is crystalline. In some embodiments, at least one of the metal, the metal alloy, the ceramic, and the semiconductor is amorphous. In some embodiments, at least one of the amorphous metal and the amorphous metal alloy is a bulk metallic glass. In one example, the porous foam 101 is produced by coating the material of the porous foam 101 onto a skeleton structure and removing the skeleton structure. In some embodiments, the skeleton structure is removed by thermal decomposition. In some embodiments, the shape of the skeleton structure forms the structure of the pores 101A. In some embodiments, the skeleton structure comprises polyurethane. Alternatively, the porous foam 101 is produced by any other method capable of forming a continuous network, a semi-continuous network, or a closed network of pores.

The pore density of the porous foam 101 correlates with an average size of the pores 101A. As such, the pore density of the porous foam 101 correlates to the size of the pockets of acoustic absorbing material 102 within the acoustic absorber 100. In some embodiments, increasing the pore density of the porous foam 101 increases the uniformity of the thermal conductivity provided by the acoustic absorber 100. In some embodiments, increasing the pore density of the porous foam 101 increases the uniformity of the acoustic attenuation provided by the acoustic absorber 100. In some embodiments, decreasing the pore density of the porous foam 101 decreases the uniformity of the thermal conductivity provided by the acoustic absorber 100. In some embodiments, decreasing the pore density of the porous foam 101 decreases the uniformity of the acoustic attenuation provided by the acoustic absorber 100.

The porosity of the porous foam 101 indicates a percentage of the porous foam 101 that is air before the addition of the acoustic absorbing material 102. The porosity of the porous foam 101 determines a percentage of the porous foam 101 that is filled by the acoustic absorbing material 102. In some embodiments, increasing the porosity of the porous foam 101 increases the acoustic attenuation of the acoustic absorber 100. In some embodiments, increasing the porosity of the porous foam 101 decreases the thermal conductivity of the acoustic absorber 100. In some embodiments, decreasing the porosity of the porous foam 101 decreases the acoustic attenuation of the acoustic absorber 100. In some embodiments, decreasing the porosity of the porous foam 101 increases the thermal conductivity of the acoustic absorber 100. As such, the specific porosities herein provide the acoustic absorber 100 are tuned to provide a sufficient thermal conductivity to prevent tissue damage and an acoustic attenuation sufficient to produce clear ultrasound images. In some embodiments, the porosity of the porous foam 101 is measured as an average porosity, a minimum porosity, or a maximum porosity. In various particular embodiments, suitable foams include those with a series of thin continuous and interconnected strands and a high degree of open pores.

In some embodiments, the porous foam 101 has a pore density of about 2 pores/cm to about 5 pores/cm, about 2 pores/cm to about 10 pores/cm, about 2 pores/cm to about 15 pores/cm, about 2 pores/cm to about 20 pores/cm, about 2 pores/cm to about 25 pores/cm, about 2 pores/cm to about 30 pores/cm, about 2 pores/cm to about 35 pores/cm, about 2 pores/cm to about 40 pores/cm, about 2 pores/cm to about 45 pores/cm, about 2 pores/cm to about 50 pores/cm, about 2 pores/cm to about 55 pores/cm, about 2 pores/cm to about 60 pores/cm, about 2 pores/cm to about 65 pores/cm, about 2 pores/cm to about 70 pores/cm, about 2 pores/cm to about 75 pores/cm, about 2 pores/cm to about 80 pores/cm, about 2 pores/cm to about 85 pores/cm, about 2 pores/cm to about 90 pores/cm, about 2 pores/cm to about 95 pores/cm, or about 2 pores/cm to about 100 pores/cm.

In some embodiments, the porous foam 101 has a pore density of about 5 pores/cm to about 10 pores/cm, about 5 pores/cm to about 15 pores/cm, about 5 pores/cm to about 20 pores/cm, about 5 pores/cm to about 25 pores/cm, about 5 pores/cm to about 30 pores/cm, about 5 pores/cm to about 35 pores/cm, about 5 pores/cm to about 40 pores/cm, about 5 pores/cm to about 45 pores/cm, about 5 pores/cm to about 50 pores/cm, 5 pores/cm to about 55 pores/cm, about 5 pores/cm to about 60 pores/cm, about 5 pores/cm to about 65 pores/cm, about 5 pores/cm to about 70 pores/cm, about 5 pores/cm to about 75 pores/cm, about 5 pores/cm to about 80 pores/cm, about 5 pores/cm to about 85 pores/cm, about 5 pores/cm to about 90 pores/cm, about 5 pores/cm to about 95 pores/cm, or about 5 pores/cm to about 100 pores/cm.

In some embodiments, the porous foam 101 has a pore density of about 10 pores/cm to about 15 pores/cm, about 10 pores/cm to about 20 pores/cm, about 10 pores/cm to about 25 pores/cm, about 10 pores/cm to about 30 pores/cm, about 10 pores/cm to about 35 pores/cm, about 10 pores/cm to about 40 pores/cm, about 10 pores/cm to about 45 pores/cm, about 10 pores/cm to about 50 pores/cm, 10 pores/cm to about 55 pores/cm, about 10 pores/cm to about 60 pores/cm, about 10 pores/cm to about 65 pores/cm, about 10 pores/cm to about 70 pores/cm, about 10 pores/cm to about 75 pores/cm, about 10 pores/cm to about 80 pores/cm, about 10 pores/cm to about 85 pores/cm, about 10 pores/cm to about 90 pores/cm, about 10 pores/cm to about 95 pores/cm, or about 10 pores/cm to about 100 pores/cm.

In some embodiments, the porous foam 101 has a pore density of about 15 pores/cm to about 20 pores/cm, about 15 pores/cm to about 25 pores/cm, about 15 pores/cm to about 30 pores/cm, about 15 pores/cm to about 35 pores/cm, about 15 pores/cm to about 40 pores/cm, about 15 pores/cm to about 45 pores/cm, about 15 pores/cm to about 50 pores/cm, 15 pores/cm to about 55 pores/cm, about 15 pores/cm to about 60 pores/cm, about 15 pores/cm to about 65 pores/cm, about 15 pores/cm to about 70 pores/cm, about 15 pores/cm to about 75 pores/cm, about 15 pores/cm to about 80 pores/cm, about 15 pores/cm to about 85 pores/cm, 15 pores/cm to about 90 pores/cm, about 15 pores/cm to about 95 pores/cm, or about 15 pores/cm to about 100 pores/cm.

In some embodiments, the porous foam 101 has a pore density of about 20 pores/cm to about 25 pores/cm, about 20 pores/cm to about 30 pores/cm, about 20 pores/cm to about 35 pores/cm, about 20 pores/cm to about 40 pores/cm, about 20 pores/cm to about 45 pores/cm, about 20 pores/cm to about 50 pores/cm, about 20 pores/cm to about 55 pores/cm, about 20 pores/cm to about 60 pores/cm, about 20 pores/cm to about 65 pores/cm, about 20 pores/cm to about 70 pores/cm, about 20 pores/cm to about 75 pores/cm, about 20 pores/cm to about 80 pores/cm, about 20 pores/cm to about 85 pores/cm, about 20 pores/cm to about 90 pores/cm, about 20 pores/cm to about 95 pores/cm, or about 20 pores/cm to about 100 pores/cm.

In some embodiments, the porous foam 101 has a pore density of about 25 pores/cm to about 30 pores/cm, about 25 pores/cm to about 35 pores/cm, about 25 pores/cm to about 40 pores/cm, about 25 pores/cm to about 45 pores/cm, about 25 pores/cm to about 50 pores/cm, about 25 pores/cm to about 55 pores/cm, about 25 pores/cm to about 60 pores/cm, about 25 pores/cm to about 65 pores/cm, about 25 pores/cm to about 70 pores/cm, about 25 pores/cm to about 75 pores/cm, about 25 pores/cm to about 80 pores/cm, about 25 pores/cm to about 85 pores/cm, about 25 pores/cm to about 90 pores/cm, about 25 pores/cm to about 95 pores/cm, or about 25 pores/cm to about 100 pores/cm.

In some embodiments, the porous foam 101 has a pore density of about 30 pores/cm to about 35 pores/cm, about 30 pores/cm to about 40 pores/cm, about 30 pores/cm to about 45 pores/cm, about 30 pores/cm to about 50 pores/cm, about 30 pores/cm to about 55 pores/cm, about 30 pores/cm to about 60 pores/cm, about 30 pores/cm to about 65 pores/cm, about 30 pores/cm to about 70 pores/cm, about 30 pores/cm to about 75 pores/cm, about 30 pores/cm to about 80 pores/cm, about 30 pores/cm to about 85 pores/cm, about 30 pores/cm to about 90 pores/cm, about 30 pores/cm to about 95 pores/cm, or about 30 pores/cm to about 100 pores/cm.

In some embodiments, the porous foam 101 has a pore density of about 35 pores/cm to about 40 pores/cm, about 35 pores/cm to about 45 pores/cm, about 35 pores/cm to about 50 pores/cm, 35 pores/cm to about 55 pores/cm, about 35 pores/cm to about 60 pores/cm, about 35 pores/cm to about 65 pores/cm, 35 pores/cm to about 70 pores/cm, about 35 pores/cm to about 75 pores/cm, about 35 pores/cm to about 80 pores/cm, 35 pores/cm to about 85 pores/cm, about 35 pores/cm to about 90 pores/cm, about 35 pores/cm to about 95 pores/cm, or about 35 pores/cm to about 100 pores/cm.

In some embodiments, the porous foam 101 has a pore density of about 40 pores/cm to about 45 pores/cm, about 40 pores/cm to about 50 pores/cm, about 40 pores/cm to about 55 pores/cm, about 40 pores/cm to about 60 pores/cm, about 40 pores/cm to about 65 pores/cm, about 40 pores/cm to about 70 pores/cm, about 40 pores/cm to about 75 pores/cm, about 40 pores/cm to about 80 pores/cm, about 40 pores/cm to about 85 pores/cm, about 40 pores/cm to about 90 pores/cm, about 40 pores/cm to about 95 pores/cm, or about 40 pores/cm to about 100 pores/cm.

In some embodiments, the porous foam 101 has a pore density of about 45 pores/cm to about 50 pores/cm, 45 pores/cm to about 55 pores/cm, 45 pores/cm to about 60 pores/cm, 45 pores/cm to about 65 pores/cm, 45 pores/cm to about 70 pores/cm, 45 pores/cm to about 75 pores/cm, 45 pores/cm to about 80 pores/cm, 45 pores/cm to about 85 pores/cm, 45 pores/cm to about 90 pores/cm, 45 pores/cm to about 95 pores/cm, or 45 pores/cm to about 100 pores/cm.

In some embodiments, the porous foam 101 has a pore density of about 2 pores/cm, about 5 pores/cm, about 10 pores/cm, about 15 pores/cm, about 20 pores/cm, about 25 pores/cm, about 30 pores/cm, about 35 pores/cm, about 40 pores/cm, about 45 pores/cm, about 50 pores/cm, about 55 pores/cm, about 60 pores/cm, about 65 pores/cm, about 70 pores/cm, about 75 pores/cm, about 80 pores/cm, about 85 pores/cm, about 90 pores/cm, about 95 pores/cm, or about 100 pores/cm, including increments therein. In some embodiments, the porous foam 101 has a pore density of at least about 2 pores/cm, about 5 pores/cm, about 10 pores/cm, about 15 pores/cm, about 20 pores/cm, about 25 pores/cm, about 30 pores/cm, about 35 pores/cm, about 40 pores/cm, about 45 pores/cm, about 50 pores/cm, about 55 pores/cm, about 60 pores/cm, about 65 pores/cm, about 70 pores/cm, about 75 pores/cm, about 80 pores/cm, about 85 pores/ cm, about 90 pores/cm, or about 95 pores/cm, including increments therein. In some embodiments, the porous foam 101 has a pore density of at most about 5 pores/cm, about 10 pores/cm, about 15 pores/cm, about 20 pores/cm, about 25 pores/cm, about 30 pores/cm, about 35 pores/cm, about 40 pores/cm, about 45 pores/cm, about 50 pores/cm, about 55 pores/cm, about 60 pores/cm, about 65 pores/cm, about 70 pores/cm, about 75 pores/cm, about 80 pores/cm, about 85 pores/cm, about 90 pores/cm, about 95 pores/cm, or about 100 pores/cm, including increments therein. In some embodiments, the pore density of the porous foam 101 is measured as an average density, a minimum density, or a maximum density.

In some embodiments, the porous foam 101 has a porosity of about 60% to about 62%, about 60% to about 64%, about 60% to about 68%, about 60% to about 70%, about 60% to about 74%, about 60% to about 78%, about 60% to about 82%, about 60% to about 86%, about 60% to about 90%, about 60% to about 98%, about 62% to about 64%, about 62% to about 68%, about 62% to about 70%, about 62% to about 74%, about 62% to about 78%, about 62% to about 82%, about 62% to about 86%, about 62% to about 90%, about 62% to about 98%, about 64% to about 68%, about 64% to about 70%, about 64% to about 74%, about 64% to about 78%, about 64% to about 82%, about 64% to about 86%, about 64% to about 90%, about 64% to about 98%, about 68% to about 70%, about 68% to about 74%, about 68% to about 78%, about 68% to about 82%, about 68% to about 86%, about 68% to about 90%, about 68% to about 98%, about 70% to about 74%, about 70% to about 78%, about 70% to about 82%, about 70% to about 86%, about 70% to about 90%, about 70% to about 98%, about 74% to about 78%, about 74% to about 82%, about 74% to about 86%, about 74% to about 90%, about 74% to about 98%, about 78% to about 82%, about 78% to about 86%, about 78% to about 90%, about 78% to about 98%, about 82% to about 86%, about 82% to about 90%, about 82% to about 98%, about 86% to about 90%, about 86% to about 98%, or about 90% to about 98%. In some embodiments, the porous foam 101 has a porosity of about 60%, about 62%, about 64%, about 68%, about 70%, about 74%, about 78%, about 82%, about 86%, about 90%, or about 98%, including increments therein. In some embodiments, the porous foam 101 has a porosity of at least about 60%, about 62%, about 64%, about 68%, about 70%, about 74%, about 78%, about 82%, about 86%, or about 90%, including increments therein. In some embodiments, the porous foam 101 has a porosity of at most about 62%, about 64%, about 68%, about 70%, about 74%, about 78%, about 82%, about 86%, about 90%, or about 98%, including increments therein.

Doped Porous Foams

In some embodiments, the porous foam 101 is doped. In some embodiments, the porous foam 101 is doped with a conductive additive. In some embodiments, the conductive additive increases the thermal conductivity of the porous foam 101. In some embodiments, the conductive additive has a higher thermal conductivity than the thermal conductivity of the porous foam 101. In some embodiments, at least about 1%, 2%, 5%, 10%, 15%, 20%, or 25%, including increments therein, of the porous foam 101 by mass is the conductive additive. In some embodiments, at most about 1%, 2%, 5%, 10%, 15%, 20%, or 25%, including increments therein, of the porous foam 101 by mass is the conductive additive.

In some embodiments, the conductive additive comprises an inorganic material. In some embodiments, the inorganic material comprises a metal, a metal alloy, a ceramic, a semiconductor, a doping agent, or any combination thereof. In some embodiments, at least one of the metal, the metal alloy, and the ceramic is crystalline. In some embodiments, at least one of the metal, the metal alloy, the ceramic, and the semiconductor is amorphous. In some embodiments, at least one of the amorphous metal and the amorphous metal alloy is a bulk metallic glass.

Acoustic Absorbing Material

In some embodiments, the acoustic absorbing material 102 comprises an inorganic material. In some embodiments, the acoustic absorbing material 102 comprises an organic material. In some embodiments, the acoustic absorbing material 102 comprises an inorganic material and an organic material. In some embodiments, the acoustic absorbing material 102 comprises a silicone. In some embodiments, the acoustic absorbing material 102 comprises a filler and a base. In some embodiments, the filler comprises an inorganic filler. In some embodiments, the filler is a particle, a platelet, a rod, or any combination thereof.

In some embodiments, an acoustic impedance of the filler is different than an acoustic impedance of the base. In some embodiments, the acoustic impedance of the filler is greater than the acoustic impedance of the base. In some embodiments, the acoustic impedance of the filler is greater than the acoustic impedance of the base by a factor of about 1.25, 1.5, 2, 3, 4, 5, 6, 7, 8, 9, 10, 20, 30, 40, 50, or more, including increments therein. In some embodiments, the acoustic impedance of the filler is greater than the acoustic impedance of the base by at least a factor of about 1.25, 1.5, 2, 3, 4, 5, 6, 7, 8, 9, 10, 20, 30, 40, 50, or more, including increments therein. In some embodiments, the acoustic absorbing material 102 has an acoustic impedance of about 0.8 MRayls to about 4.0 MRayls. In some embodiments, the acoustic absorbing material 102 has an acoustic impedance of about 0.8 MRayls to about 1.5 MRayls. In some embodiments, the acoustic absorbing material 102 has an acoustic impedance of about 1.5 MRayls to 2.5 MRayls. In some embodiments, the acoustic absorbing material 102 has an acoustic impedance of at least about 10, 12, 14, 16, 18, 20, 24, 28, 32, 36, or 40 MRayl, including increments therein. In some embodiments, the filler has an acoustic impedance of at least about 10, 12, 14, 16, 18, 20, 24, 28, 32, 36, 40, 50, 60, 70, 80, 90, 100, or more, including increments therein. In some embodiments, the base material has an acoustic impedance of at least about 10, 12, 14, 16, 18, 20, 24, 28, 32, 36, or 40 MRayl, including increments therein.

Method of Forming a Thermally Conductive Acoustic Absorber

Another aspect provided herein is a method of forming a thermally conductive acoustic absorber for a transducer, the absorber comprising: receiving a porous foam having a plurality of pores; and saturating at least a portion of the plurality of pores of the porous foam with an acoustic absorbing material. In some embodiments, saturating the pores of the porous foam with an acoustic absorbing material comprises: drawing the acoustic absorbing material into the plurality of pores of the porous foam under vacuum; pressing the acoustic absorbing material into the plurality of pores of the porous foam under pressure, heating the absorbing material, heating the porous foam, or any combination thereof.

In some embodiments, the specific acoustic absorbing material as well as the porosity of the porous foam enables the acoustic material to saturate a majority of the pores of the porous foam. In some embodiments, at least about 70%, 75%, 80%, 85%, 90%, 95%, 99%, or more, including increments therein, or more of the porous foam by volume is saturated by the acoustic absorbing material. In some embodiments, an increased saturation of the porous foam produces an acoustic absorber with a greater acoustic attenuation. In some embodiments, the specific composition of the acoustic material, the porous foam, or both enable the high saturation percentage of the acoustic absorber. In some embodiments, the porosity, the pore density or both of the porous foam enable the high saturation percentage of the acoustic absorber. In particular embodiments, the porous foam is substantially saturated or saturated by the acoustic absorbing material.

Acoustic Absorber Performance

In some embodiments, the thermally conductive acoustic absorber has a thermal conductivity of at least 1, 2, 3, 4, 5, 6, 7, 8, 9, 10, 15, or 20 W/mK, including increments therein. In some embodiments, the thermal conductivity of the acoustic absorber is measured as an average conductivity, a minimum conductivity, or a maximum conductivity.

In some embodiments, the acoustic absorber is coupled to the transducer, an application-specific integrated circuit (ASIC), a PCB, or any combination thereof. In some embodiments, the strength of the acoustic absorber imparted by its specific materials and structure, enable the acoustic absorber to be directly bonded to the transducer, the application-specific integrated circuit (ASIC), the PCB, or any combination thereof. In some embodiments, the acoustic absorber is rigid, and does not significantly deflect under a shear and/or normal force. In some embodiments, the acoustic absorber is semi-rigid and is deflected by a shear and/or normal force.

Figure 3:
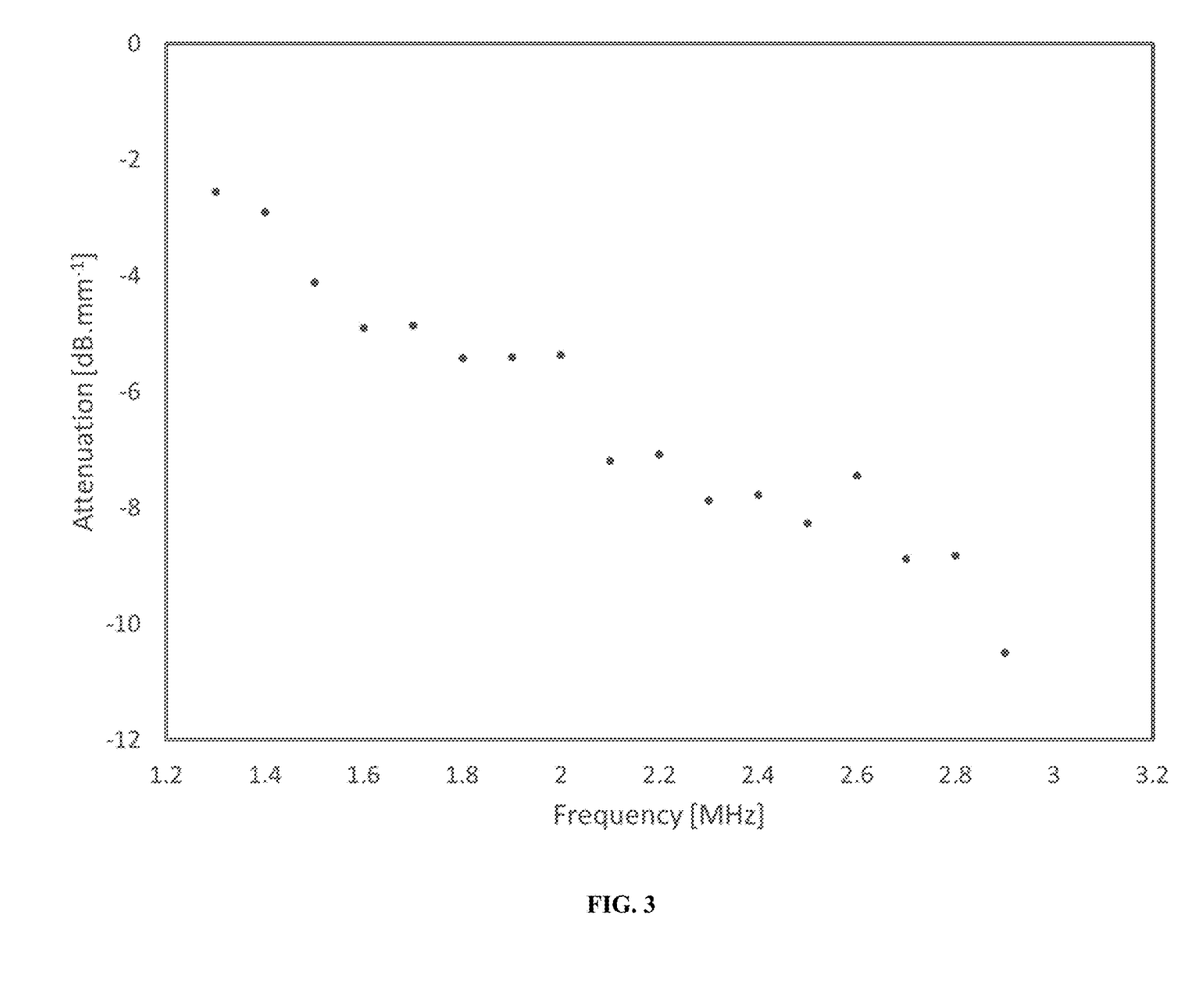
FIG. 3 shows an attenuation graph of a 90% porous copper foam filled with a silicone acoustic absorbing material, per an embodiment herein.
Figure 4:
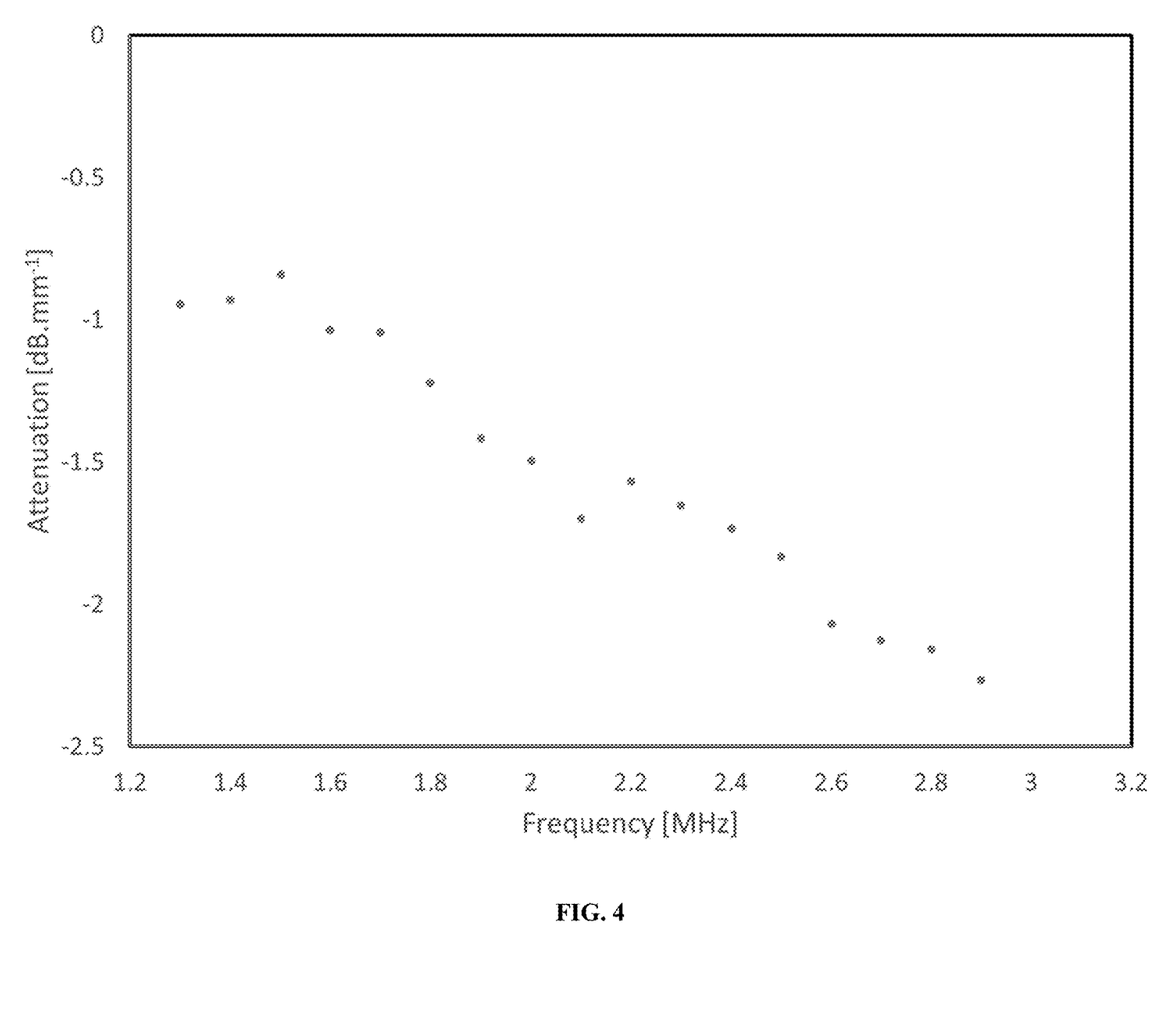
FIG. 4 shows an attenuation graph of the silicone acoustic absorbing material, per an embodiment herein.

FIG. 3 shows an attenuation graph of a 90% porous copper foam filled with a silicone acoustic absorbing material and FIG. 4 shows an attenuation graph of just the silicone acoustic absorbing material. In some embodiments, the acoustic attenuation attained by the acoustic absorber, per FIG. 3, is greater than the acoustic attenuation of the filler alone, per FIG. 4. As shown per FIG. 3, the acoustic absorber attenuates a signal having frequency of about 1.2 MHz at a pressure of about −2 dB/mm and attenuates a signal having a frequency of about 3 MHz at a pressure of about −11 dB/mm. The silicone acoustic material, per FIG. 4, attenuates a signal having frequency of about 1.2 MHz at a pressure of about −0.6 dB/mm and attenuates a signal having a frequency of about 3 MHz at a pressure of about −2.25 dB/mm.

In some embodiments, the acoustic absorber in FIG. 3 attenuates a signal having a frequency of 1.2 MHz at an attenuation rate of at about −1.5 dB/mm, −2 dB/mm, −2.5 dB/mm, −3 dB/mm, −3.5 dB/mm, −4 dB/mm, or more, including increments therein. In some embodiments, the acoustic absorber attenuates a signal having a frequency of 3 MHz at an attenuation rate of at about −5 dB/mm, −6 dB/mm, −7 dB/mm, −8 dB/mm, −9 dB/mm, −10 dB/mm, −11 dB/mm, −12 dB/mm, −14 dB/mm, −16 dB/mm, −18 dB/mm, −20 dB/mm, or more, including increments therein.

Ultrasound Probes

Figure 5:
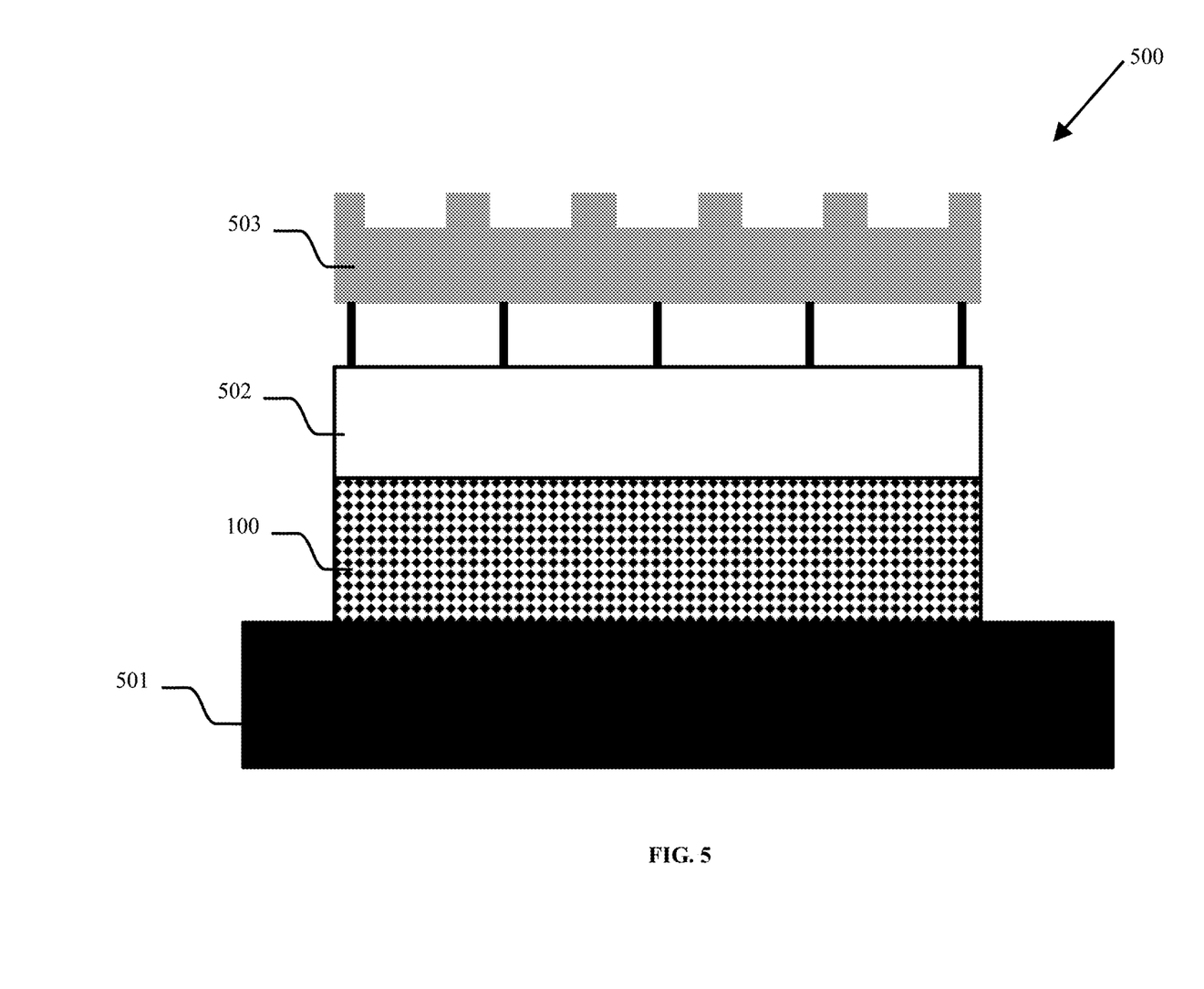
FIG. 5 shows an illustration of a first exemplary ultrasound probe, per an embodiment herein.

Provided herein per FIG. 5, is an ultrasound probe 500 comprising a printed circuit board (PCB) 501, an application-specific integrated circuit (ASIC) 502, an ultrasound transducer 503 (e.g., a PMUT, a CMUT, etc.), and a thermally conductive acoustic absorber 100. As shown in FIG. 5, the acoustic absorber 100 is mounted between the PCB 501 and the ASIC 502. In some embodiments, the ultrasound probe 500 comprises a plurality of PCBs 501, wherein the thermally conductive acoustic absorber 100 is mounted between the ASIC 502 and one or more of the plurality of PCBs 501. In some embodiments, the high acoustic energy absorption of the thermally conductive acoustic absorber 100 provides enhanced acoustic attenuation such that the transducer produces high-quality medical ultrasound images. In some embodiments, the high thermal conductivity of the acoustic absorber 100 draws heat from the transducer to prevent the transducer from exceeding the FDA thermal limit for the probe. In some embodiments, an optional acoustic reflector (high acoustic impedance reflector) is mounted between the ASIC 502 and acoustic absorber 100, to reflect at least a portion of acoustic energy back toward the ultrasound transducer 503, before any remaining acoustic energy reaches the acoustic absorber 100.

Figure 6:
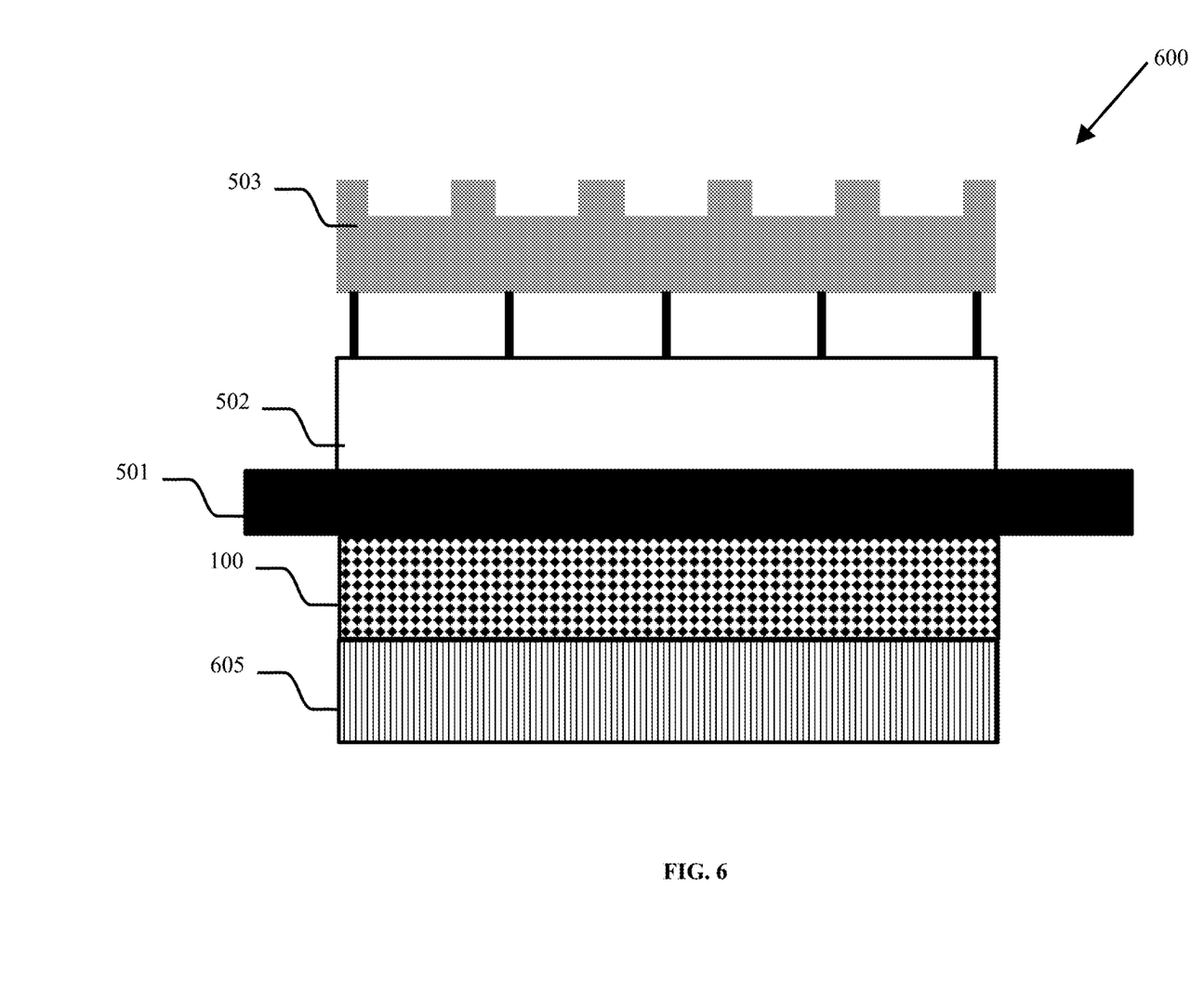
FIG. 6 shows an illustration of a second exemplary ultrasound probe, per an embodiment herein.

Provided herein as an alternative embodiment per FIG. 6, is an ultrasound probe 600 comprising a printed circuit board (PCB) 501, an application-specific integrated circuit (ASIC) 502, an ultrasound transducer 503, and a PCB heatsink 605 coupled to the PCB 501, wherein the acoustic absorber 100 is mounted between the PCB 501 and the PCB heatsink 605. In some embodiments, the ultrasound probe 600 comprises two or more acoustic absorbers 100. In some embodiments, at least one of the two or more acoustic absorbers 100 is mounted between the PCB 501 and the ASIC 502, and wherein at least one of the two or more acoustic absorbers 100 is mounted between the PCB 501 and the PCB heatsink 605. In some embodiments, an optional acoustic reflector (high acoustic impedance reflector) is mounted between the PCB 501 and the acoustic absorber 100, to reflect at least a portion of acoustic energy back toward the ultrasound transducer 503, before any remaining acoustic energy reaches the acoustic absorber 100.

In some embodiments, the acoustic absorber 100 has a sufficient strength to allow connection by, for example, adhering to the ASIC 502 and the PCB 501. In some embodiments the acoustic absorber 100 is connected to the ASIC 502, the PCB 501, or both. In some embodiments the acoustic absorber 100 is connected to the ASIC 502, the PCB 501, or both by an adhesive.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the term "about," in reference to a percentage, refers to an amount that is greater or less the stated percentage by 10%, 5%, or 1%, including increments therein.

As used herein, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

As used herein, the term "continuous network of pores" refers to a pore structure, wherein at most a portion of the pores in the pore structure are closed. A closed pore is surrounded by its structure preventing ingress or egress of gases, liquids, or solids.

As used herein, the term "semi-continuous network of pores" refers to a pore structure, wherein a portion of the pores in the pore structure are closed.

As used herein, the term "partially open network of pores" refers to a pore structure, wherein at least portion of the pores in the pore structure are closed.

As used herein, the term "stochastic" refers to a foam structure whose porosity distribution is random or disordered.

As used herein, the term "regular" refers to a foam structure whose porosity distribution is uniform or ordered.

As used herein, the term "porosity" refers to a measure of the percentage of a foam that is formed of empty space.

As used herein, the term "thermal conductivity" is a measurement of a material's ability to conduct heat. In some embodiments, the thermal conductivity is a minimum impedance, an average impedance, or a maximum thermal conductivity of a material. In some embodiments, the thermal conductivity of a material is measured by any known method.

As used herein, the term "crystalline" refers to a compound, wherein at least a portion of the compound has a structure of a crystal.

As used herein, the term "amorphous" refers to a compound wherein at least a portion of the compound has an irregular internal structure.

As used herein, the term "acoustic impedance" is a measure of the opposition that a material or combination of materials presents to the acoustic flow resulting from an acoustic pressure applied to the system. In some embodiments, impedance is measured in MRayls. In various embodiments, the impedance is a minimum impedance, an average impedance, or a maximum impedance of a material. In some embodiments, the impedance of a material is measured by any known method.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. An ultrasound probe comprising:
   (a) a printed circuit board (PCB);
   (b) an application-specific integrated circuit (ASIC) coupled to the PCB directly above the PCB;
   (c) a piezoelectric micromachined ultrasound transducer (pMUT) coupled to the ASIC; and
   (d) a thermally conductive acoustic absorber mounted between the PCB and a heatsink, the thermally conductive acoustic absorber comprising:
      i) an acoustic absorber comprising a porous copper foam having a plurality of pores; and
      (ii) an acoustic absorbing material comprising an epoxy and tungsten particle mixture within at least a portion of the plurality of pores of the porous copper foam.

2. The ultrasound probe of claim 1, wherein the pores form a continuous network.

3. The ultrasound probe of claim 1, wherein the pores form a semi-continuous network.

4. The ultrasound probe of claim 1, wherein the pores are partially closed.

5. The ultrasound probe of claim 1, wherein the pores are closed.

6. The ultrasound probe of claim 1, wherein the porous foam has a pore density of about 2 pores/cm to about 100 pores/cm.

7. The ultrasound probe of claim 1, wherein the porous foam has a porosity of about 60% to about 98%.

8. The ultrasound probe of claim 1, wherein the porous foam comprises a cellular material, a sponge material, or both.

9. The ultrasound probe of claim 1, wherein the porous foam comprises an inorganic material with a porous foam structure.

10. The ultrasound probe of claim 9, wherein the inorganic material comprises a metal, a metal alloy, a ceramic, a semiconductor, a composite, or any combination thereof.

11. The ultrasound probe of claim 10, wherein the inorganic material is at least partially crystalline.

12. The ultrasound probe of claim 1, further comprising an acoustic reflector mounted between the PCB and the acoustic absorber to reflect at least a portion of acoustic energy back toward the ultrasound transducer before any remaining acoustic energy reaches the acoustic absorber.

13. The ultrasound probe of claim 1, wherein the thermally conductive acoustic absorber is directly bonded to the PCB and the heatsink.

14. The ultrasound probe of claim 1, wherein the acoustic absorber reduces reflections of acoustic energy off the heatsink and wherein a thermal conductivity of the acoustic absorber is sufficient to act as a heatsink.

15. The ultrasound probe of claim 1, wherein the pMUT is coupled to the ASIC through a plurality of pillars.

16. An ultrasound probe comprising:
   (a) a printed circuit board (PCB);
   (b) an application-specific integrated circuit (ASIC) coupled to the PCB;
   (c) a piezoelectric micromachined ultrasound transducer (pMUT) coupled to the ASIC; and
   (d) a thermally conductive acoustic absorber mounted between the PCB and the ASIC, the thermally conductive acoustic absorber comprising:
      (i) an acoustic absorber comprising a porous copper foam having a plurality of pores; and
      (ii) an acoustic absorbing material comprising an epoxy and tungsten particle mixture within at least a portion of the plurality of pores of the porous copper foam.

17. The ultrasound probe of claim 16, wherein the pMUT is coupled to the ASIC through a plurality of pillars.

18. An ultrasound probe comprising:
(a) a printed circuit board (PCB);
(b) an application-specific integrated circuit (ASIC) coupled to the PCB;
(c) a micromachined ultrasound transducer (MUT) coupled to the ASIC; and
(d) a thermally conductive acoustic absorber comprising:
  (i) a porous foam having a plurality of pores that form a semi-continuous network; and
  (ii) an acoustic absorbing material within at least a portion of the plurality of pores of the porous foam.

19. The ultrasound probe of claim 18, wherein the porous foam comprises a copper foam.

20. The ultrasound probe of claim 19, wherein the acoustic absorbing material comprises an epoxy and an inorganic filler.

21. The ultrasound probe of claim 20, wherein the inorganic filler comprises tungsten.

22. The ultrasound probe of claim 18, wherein the porous foam comprises an inorganic material with a porous foam structure.

23. The ultrasound probe of claim 18, wherein the MUT comprises a piezoelectric micromachined ultrasound transducer.

24. The ultrasound probe of claim 18, wherein the MUT is coupled to the ASIC through a plurality of pillars.

25. The ultrasound probe of claim 18, wherein the PCB and the MUT are coupled to different sides of the ASIC.

* * * * *